(12) United States Patent
Slade

(10) Patent No.: US 6,513,725 B1
(45) Date of Patent: Feb. 4, 2003

(54) DISPENSING APPARATUS FOR A VOLATILE LIQUID

(76) Inventor: Brian Slade, 20 Star Road, Ashford, Kent (GB), TN24 8BX (*) Notice: Subject to any disclaimer, the term of this patent is extended or adjusted under 35 U.S.C. 154(b) by 0 days.

(21) Appl. No.: 09/786,686

(22) PCT Filed: Sep. 8, 1999

(86) PCT No.: PCT/GB99/02991

§ 371 (c)(1),
(2), (4) Date: May 8, 2001

(87) PCT Pub. No.: WO00/13925

PCT Pub. Date: Mar. 16, 2000

(30) Foreign Application Priority Data

Sep. 8, 1998 (EP) .............................. 98307253

(51) Int. Cl.[7] .............................. A24F 25/00; A61L 9/04
(52) U.S. Cl. .............................. 239/34; 239/43; 239/44; 239/55
(58) Field of Search .............................. 239/34, 43, 44, 239/46, 50, 51, 55, 57, 145, 154, DIG. 12, 56, 60; 222/402.21, 402.22, 402.23, 405, 164

(56) References Cited

U.S. PATENT DOCUMENTS

| | | | | |
|---|---|---|---|---|
| 3,722,760 A | * | 3/1973 | Hug | ............... 222/402.22 |
| 3,805,856 A | * | 4/1974 | McLennand | ............... 141/286 |
| 4,157,787 A | * | 6/1979 | Schwartz | ............... 239/56 |
| 4,294,410 A | * | 10/1981 | Gueret | ............... 239/577 |
| 4,304,342 A | * | 12/1981 | Morane | ............... 222/402.23 |
| 4,352,461 A | | 10/1982 | Orta et al. | |
| 4,501,409 A | * | 2/1985 | Hill et al. | ............... 251/354 |
| 4,632,310 A | | 12/1986 | Konicek | |
| 4,753,389 A | | 6/1988 | Davis | |
| 5,518,179 A | * | 5/1996 | Humberstone et al. | .. 239/102.2 |
| 5,725,152 A | * | 3/1998 | Akyu | ............... 239/45 |
| 5,749,519 A | * | 5/1998 | Miller | ............... 239/44 |
| 5,749,520 A | * | 5/1998 | Martin et al. | ............... 239/44 |
| 5,875,968 A | * | 3/1999 | Miller et al. | ............... 239/44 |
| 6,039,266 A | * | 3/2000 | Santini | ............... 239/60 |

FOREIGN PATENT DOCUMENTS

| | | |
|---|---|---|
| CH | 668 536 A5 | 1/1989 |
| CH | 668 536 | 1/1989 |
| EP | 0 501 601 | 9/1992 |
| FR | 206950305 | 9/1992 |
| FR | 2 695 305 | 3/1994 |

* cited by examiner

Primary Examiner—Michael Mar
Assistant Examiner—Davis Hwu
(74) Attorney, Agent, or Firm—Pillsbury Winthrop LLP

(57) ABSTRACT

A dispenser for a volatile liquid is intended to be used in a vehicle. It comprises a substantially closed conical container (2) for the liquid, and a pair of plates (14, 28) closing the top of the container form between them a capillary interface (88) leading to a disseminating porous element (42). While the vehicle is in movement, liquid is thrown upwards and outwards by accelerations of the vehicle to the plates and so to drawn through the capillary passages at the interface to reach the porous element. The container is pivoted at its lower region to be tiltable through a similar angle to tilt of the liquid surface, so that all the liquid can reach the plates and so be dispensed.

18 Claims, 3 Drawing Sheets

DISPENSING APPARATUS FOR A VOLATILE LIQUID

Figure 1:
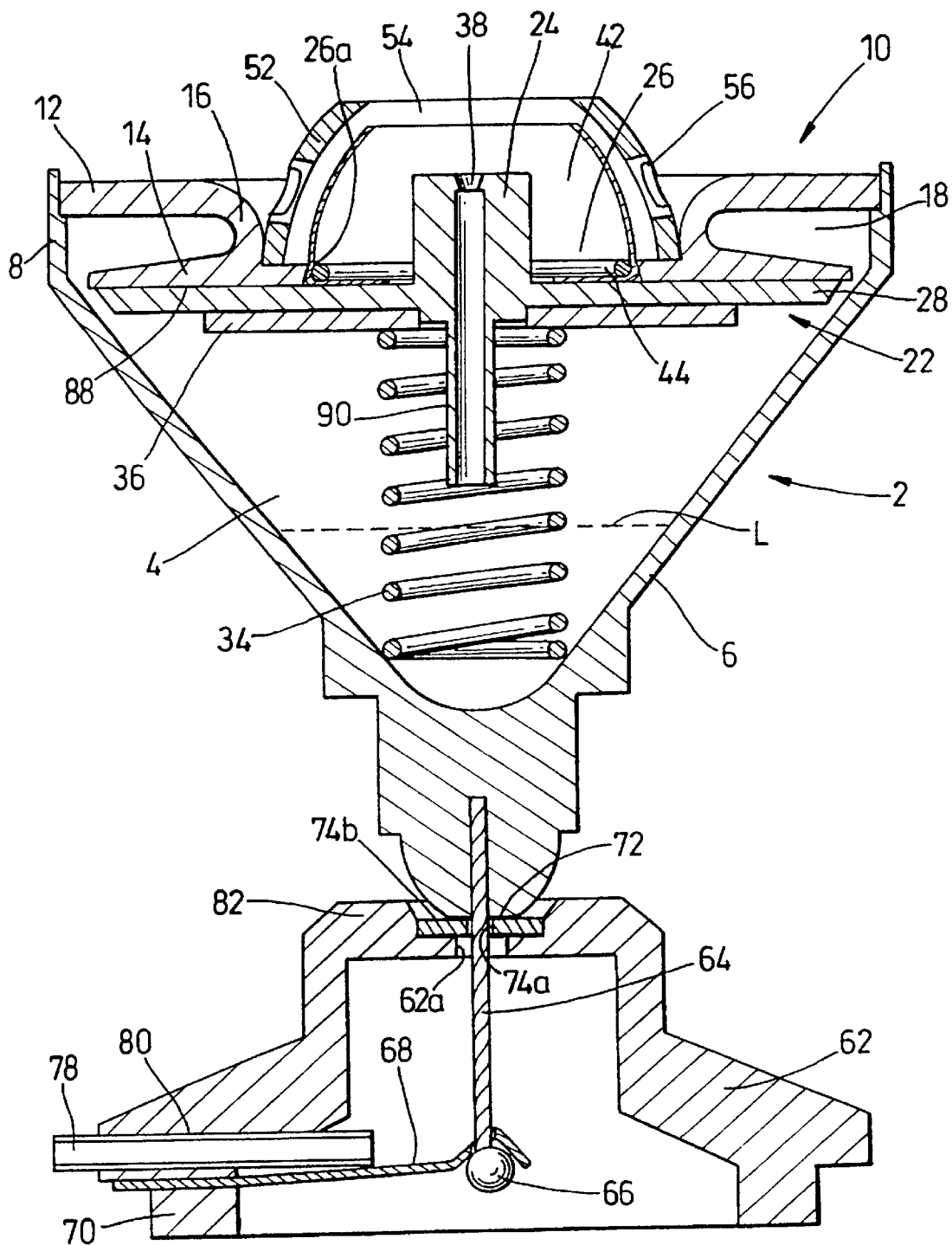

The invention relates to apparatus for dispensing volatile liquids, such as fragrances and air freshening substances. It is particularly concerned with such dispensing apparatus for use in vehicles, especially road vehicles.

One problem encountered with the use of liquid fragrances and fresheners in road vehicles is that there are frequent periods, often lengthy, when the vehicle is not in use but the liquid continues to volatilise. If the vehicle interior is completely closed, as is often the case when the vehicle is not in use, high concentrations of the volatilised material can accumulate in the atmosphere in the vehicle, especially as the closure of the interior frequently results in a considerable temperature increase. The result can be unpleasant for the occupants when the vehicle is next used, and is wasteful of the material being dispensed.

It is an object of the invention to at least ameliorate these problems.

According to one aspect of the invention, there is provided a dispensing apparatus for a volatile liquid comprising a container having a substantially closed interior space for the liquid and at least one capillary passage for communication with the exterior extending from an upper region of the interior space adjacent an upwardly extending wall or partition of the container, whereby liquid displaced onto said wall or partition to reach said at least one capillary passage can be drawn therethrough to be released from the container.

With such an apparatus located in a moving vehicle, the inertia of the liquid causes it to be displaced in the container as the vehicle changes speed or direction. By arranging that the liquid then reaches said at least one capillary passage it can be dispensed from the container while the vehicle is moving.

Preferably, the container is mounted on a support in an upright position but is tiltable thereon by a transverse inertia force in the same direction as the direction of displacement of the liquid. The container can thus be itself displaceable by inertia forces generated during the motion of the vehicle, so that its tilting will assist the displacement of the liquid towards said at least one capillary passage.

According to another aspect of the invention, a dispensing apparatus is provided for a volatile liquid, comprising a container with substantially closed interior space having at least one capillary passage opening into an upper peripheral region of the interior space for communication with the exterior, and a mounting on which the container is tiltably supported, return means acting between the mounting and the container urging the container to an upright position on the mounting, the container being able to tilt against the action of said return means under the influence of inertia forces acting transversely upon it.

Preferably, the container is in the form of a bowl with a side wall sloping upwards and outwards from a central bottom region towards said at least one capillary passage. The angle of slope to the horizontal will normally be at least 15°, but can be considerably greater. In particular, if the container is arranged to be tiltable, an angle of slope of between 30° and 60° is preferred. At least the upper region of the side wall can conveniently have a substantially conical shape.

In a dispenser according to the invention, it is convenient to arrange said at least one capillary passage to open into the interior of the container adjacent around substantially the entire periphery of the container upper region so that said passage or passages can collect liquid displaced in any direction from the lower region in which it is normally at rest.

In a particularly convenient arrangement, the container is rotationally symmetrical and a pair of abutting or closely adjacent plates extending close to the periphery of the container upper region form said capillary passage or passages at their interface, so that liquid reaching the interface at any point around the periphery is drawn through the passage or passages inwards by the capillary action to a central upper region of the container from where it can escape to the exterior. Preferably, at the outlet end of the passage or passages there are distribution means to assist the volatilisation and dispersion of the liquid.

Any ability of the container to tilt in response to disturbing forces generated by the movement of the vehicle is preferably limited, to limit the exposure of the liquid to said capillary passage or passages. This maximum angle of tilt may be related to any initial slope of the wall or partition along which the liquid travels;

desirably, the tilt is limited to give the container wall a final slope at a minimum angle of not substantially less than 15° to the horizontal, and preferably not substantially less than 25°. The liquid will of course also be tilted and it may be arranged that under normal manoeuvring conditions the liquid surface tilt will approximately correspond to the final angle of slope of the container wall adjacent the capillary passage.

The depth of liquid at rest in the container is another factor, and in a further preferred feature, means are provided to limit the filling level of the container to some distance below said at least one capillary passage, so that the displaced liquid does not reach the passage too easily due to overfilling.

Figure 2:
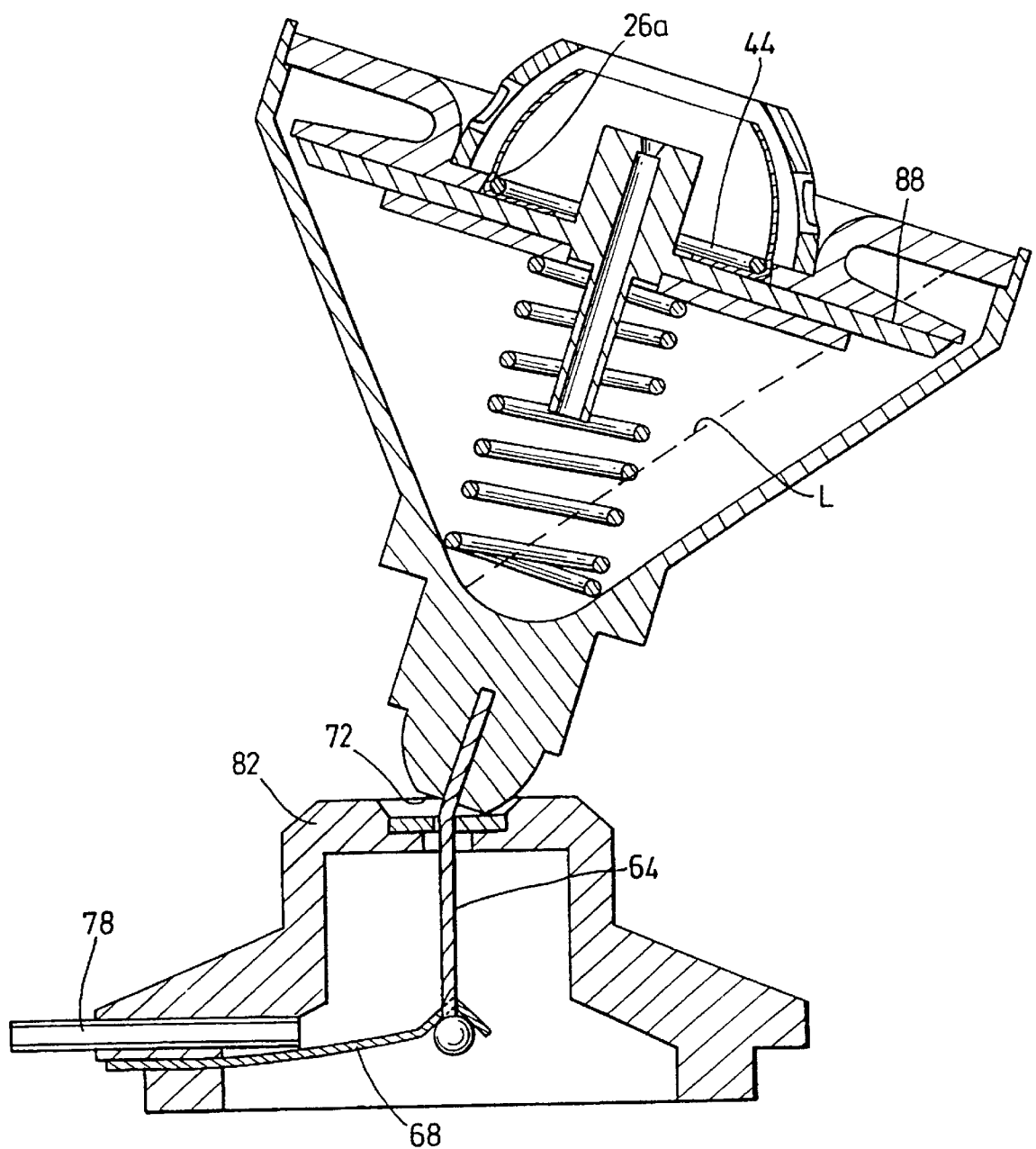
Figure 3:
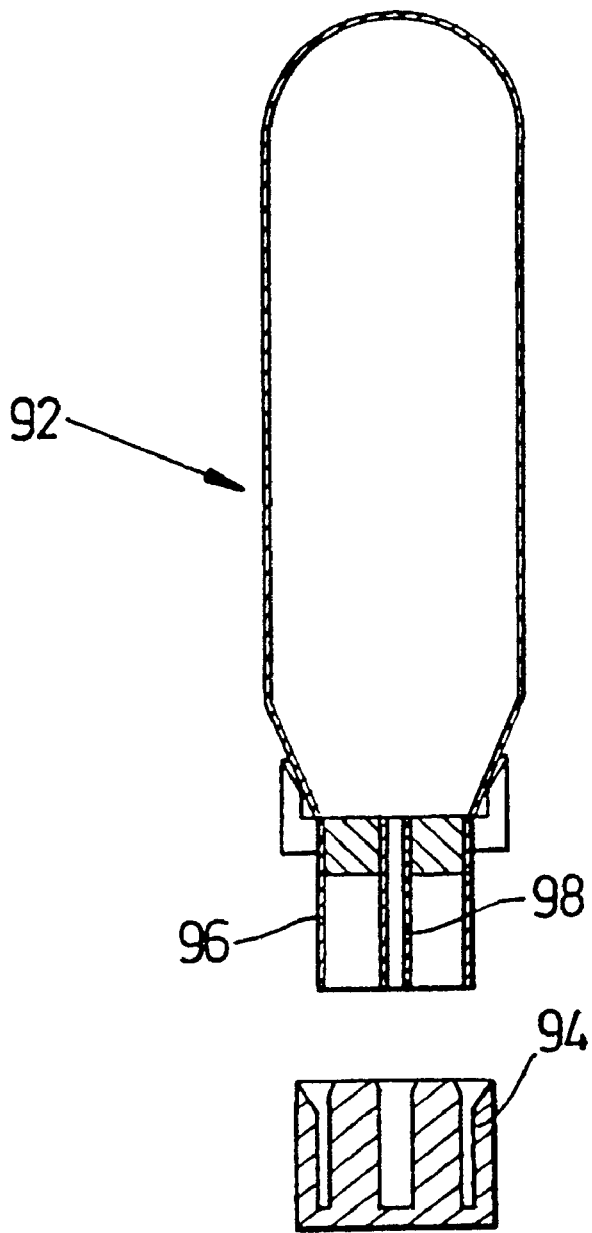

By way of example, an embodiment of the invention will be described in more detail with reference to the accompanying drawings, in which:

FIG. 1 is an axial sectional view of an apparatus according to the invention at rest, FIG. 2 is a similar view showing the apparatus tilted when in use, and FIG. 3 is a sectional illustration of a refill capsule for the apparatus of FIGS. 1 and 2.

The apparatus comprises a rotationally symmetrical container 2 having a bowl-form interior 4 widening upwards from a relatively narrow lower region. In the illustrated example the container thus has a generally conical form, the side wall 6 being inclined at an angle of about 50° to the horizontal. Continuing from the inclined side wall 6, the container terminates at the top with a short cylindrical wall 8.

Fitting within the wall 8 is a top closure 10 comprising an upper wall 12 sealed at its outer edge to the wall and a lower wall 14 spaced from the upper wall by an integral, downwardly turned inner wall 16. The top closure walls, with the wall 8, enclose an annular space 18 sealed from the exterior but open to the remainder of the interior through a narrow gap between the container wall and the closure lower wall 14.

An inner member 22 comprising a central boss 24 projecting through a central opening 26 in the annular lower wall 14 has an integral disc-form skirt 28 which, like the closure lower wall 14, extends close to the container inner wall. The skirt 28 is urged into contact with the lower wall 14 by a spring 34 compressed between the bottom of the container and a metal bearing plate 36 that abuts the skirt 28. In the boss 24 is a filling aperture 38 through which the liquid to be dispensed can be put into the container.

The container 2, the top closure 10 and the inner member 22 may be moulded from a plastic material such as Deirin (TM). The metal bearing plate 36 spreads the spring load acting on the skirt 28 to ensure that there is close contact between a substantial area of the closure lower wall 14 and the inner member skirt 28, so that their abutting faces act as capillary faces, ie. capillary passages being formed between them, as will be described below.

The closure lower wall 14 extends inwardly past the inner wall 16 but the relatively large central opening 26 is overlapped by the inner region of the skirt 28. The inner edge 26a of the lower wall around the aperture 26 is chamfered to form an acute-angled recess with the adjoining face of the skirt 28.

A porous sheet element 42 is secured in the central aperture 26 of the closure lower wall by a spring ring 44 fitting into the recess. The sheet element 42 is initially a flat disc with a central hole through which the boss 24 projects. When the spring ring 44 is put in place, it forces the element 42 into the acute-angled recess and the abutting edge 26a of the aperture forces the outer margins of the element 42 upwards into a generally curved pleated shape.

In the present example, the sheet element 42 is made of Unisorb base paper U1 45 gm/m² manufactured by Devon Valley Industries Limited of Exeter, Devon, but any sheet material having the required degree of porosity and stability of shape can be used, preferably having a low bulk as a thin sheet will hold less liquid at any instant.

A protective cover 52, secured to the annular shoulder formed between the lower and inner walls 14,16 lies over the sheet element 42. A large central aperture 54 in the cover is located over the boss 24. A series of further apertures 56 are provided in the cover 54, overlying the outer margins of the sheet element 42.

The container is mounted on a base support 62 to which it is attached by a flexible connecting element 64, e.g. a nylon cord. The cord 62 has a ball end 66 that is passed through the central bore 62a on assembly and is held in the free end of a leaf spring 68 projecting into the hollow support 62 from the bottom rim 70 of the support. The spring 68 applies a tension to the element 64 to hold the container normally upright, with its bottom face 72 against a bearer plate 74 set into a recess 76 in the top face of the support 62. The container bottom face 72 and the contacting top face 74b of the bearer plate 74 are surfaces of revolution concentric to each other. The tension element 64 passes through their central axis and is maintained in that central position by a clearance hole 74a in the plate in which it can slide freely. Flexure of the spring by the tension in the connecting element forces the spring against a screw 78 threaded into a bore 80 to extend generally parallel to the spring, close to its upper face. Adjustment of the screw inwards and outwards (see FIGS. 1 and 2), respectively increases and reduces the tension in the connecting element.

The abutting top and bottom faces 72, 74b are so formed that, in a position of rest in which the container and support are concentric with each other, as shown in FIG. 1, they make contact over a disc-form area in a central region extending some distance radially from the central tension element. Outwardly from that area there is an intermediate annular region in which the faces diverge from each other at a progressively increasing rate. Beyond that annular region, there is an outer region in which the distance between the faces lessens. In the illustrated configuration, these characteristics are obtained by using a plate 74 having a flat top face 74b surrounded by upstanding rim 82 of the recess 76, and forming the container bottom as a hemisphere with the contact face 72 as a central flat around the tension element 64.

As already described, the apparatus is intended to be mounted in a vehicle to act as a dispenser for a volatile liquid such as a fragrance. The base support 62 is fixed in place with the central axis of the apparatus preferably vertical, but in any event in a more or less upright rest position, as will be clear from the following description of its operation.

In use, the liquid fragrance fills the lower region of the container to a level L when the apparatus is in the rest position shown in FIG. 1. In this position the liquid, when it vaporises, can escape only through the small filling aperture 38 in the inner member 22 from which it will dissipate at so slow a rate as not to be hardly noticeable, if at all. However, when the vehicle is driven, from changes of speed and of direction of travel its motion will create inertia forces in the liquid and the container in all directions transverse to the central axis of the container. The liquid will flow to one side or the other of the container in direct dependence to the inertia force it experiences, towards a peripheral region of the capillary faces of the plates 14,28. Because of the rotational symmetry of the container and the plates 14,28 this effect is independent of the direction of tilt.

The central flat contact face 72 bearing on the support 62 will initially resist any lateral inertia forces acting on the container 2, which tend to displace the container in the same direction since its centre of gravity is above the support. However, once those forces exceed a minimum value required to allow it to overcome the restoring tension in the flexible element, the container will tilt on the support to an increasing degree in dependence upon the force experienced, until it contacts the rim of the support. This occurs at an angle of tilt of the container axis of about 25° and preferably not more than 30° to the vertical. The tilting of the container complements the displacement of the liquid under its own inertia, so bringing the liquid more readily into contact with the two capillary plates at a peripheral region. In the example of the illustrated embodiment, the apparatus is arranged for an expected angle of tilt of the liquid surface of some 25° to 30° to the horizontal. The tilt of the liquid and of the wall of the container on which it rests are thus substantially equal as illustrated in FIG. 2.

While the two plates 14,28 are forced into contact with each other, they will not have perfect planar matching faces, so that there are passages in the interface 88 between the plates into which liquid can be drawn by capillary action. Liquid reaching the outer edges of the plates is therefore drawn across the interface of the plates 14,28 to the inner edge 26a where it is adsorbed by the porous sheet element 42 in the acute-angled recess. The liquid thus spreads over the surface of the sheet element 42 to be exposed to the external atmosphere, in particular over the upstanding generally cylindrical margin of the element, from where the fragrance vaporises readily. The disseminating sheet element 42 will continue to draw liquid from the recess as long as it is supplied by the capillary action in the interface 88 between the plates 14,28. As soon as the disturbing force ceases, however, allowing the container and its contents to return towards the rest position, the supply of liquid ceases.

Because of the close contact between the plates 14,28, the capillary passages contain only a very small volume of liquid so the fragrance quickly reaches the element 42. Accordingly, there is a relatively rapid response in the initial release of the fragrance due to liquid being taken up by the plates. Similarly, because only a small amount of material can be taken up by the plates 14,28 and porous sheet element 42, very little need be released when the journey is ended and the dispenser is no longer subject to tilting disturbances, so that the fragrance is used economically.

When the vehicle is at rest, it is of course possible that it is on an incline so that the apparatus is tilted even though the container has been centralised on the base support. However, in the illustrated example the side wall of the container is sufficiently steep to prevent the liquid reaching the capillary passages under any probable static conditions.

While the apparatus is not mounted in place it is possible that it could be mishandled and turned upside down. Should that happen, the liquid in the container will run into the annular space 18, so reducing any risk that the capillary passages between the plates 14,28 will be flooded and excess liquid will spill from the container. The liquid is in any case prevented from spilling from the filling opening 38 because the opening communicates with the interior through an extension tube 90 projecting downwards some distance below the lower skirt 28. The presence of the tube 90 also makes it difficult to overfill the container. Limiting the upper level of the liquid in the container at any time also limits the risk of dispensing liquid unnecessarily when the vehicle is parked on an incline.

The container 2 can take other shapes than that shown. The small base and sloping sides of the generally conical form shown has the advantage that most if not all of the liquid in the container is able eventually to run to the outer margins of the capillary plates under the action of the lateral disturbing forces experienced during motion of the vehicle, so there need be little or no wastage.

Similarly the angle of tilt required for the container will depend to some extent on the shape of the container. If a very shallow container is employed, for example if the side wall is inclined at a relatively small angle to the horizontal it is possible to rely solely on the lateral displacement of the liquid under its own inertia. Under normal driving conditions, it can be assumed that the inertia forces on the liquid can tilt its surface some 20–30° to the horizontal. If the container were rigidly fixed in place, therefore, the side wall would require a similar slope to allow most if not all the liquid to be dispensed. A significantly smaller angle of slope should be avoided however, to limit unwanted dispersal of liquid when the vehicle is parked on an incline.

By making the container tiltable in use, all risk of the liquid reaching the capillary plates, when the vehicle is parked, can be avoided, if the slope of the side wall is sufficient. To achieve this effect, it is desirable, in general, that the container has a side wall that slopes in its upper region extending between the surface of the liquid at rest and the capillary plates, at an angle of not less than 25° and preferably at least 30°, while the container should be capable of tilting through an angle of at least 10°, and preferably at least 20°, from its rest position. It will be understood, moreover, that the ability of the container to tilt can also allow the occupant of the vehicle to operate the dispenser manually, if so desired, when the vehicle is parked.

Of course, the steepness of the container side wall keeps the liquid from the capillary plates only while the vehicle is at rest and the tilting capability under acceleration, whether sideways or fore and aft, can be arranged to counteract the initial incline of the side wall completely. By arranging that expected incline of the liquid surface to the horizontal is at least equal the tilted incline of the side wall, as shown in FIG. 2, no residue of liquid is left that cannot reach the plates 14,28.

To facilitate refilling it is preferred to provide single-charge flexible wall capsules 92 of the form shown in FIG. 3. When the capsule sealing cap 94 is removed, a skirt 96 surrounding an outlet tube 98 can be located over the boss 24, so that the tube 98 extends into the filling opening 38 and the capsule is then squeezed to discharge its contents. Such a capsule carrying a charge of, e.g. 3.5 ml of liquid, will fill the container to the level L shown in FIG. 1, somewhat below the level of the extension tube.

Many modifications of the apparatus described are possible within the scope of the invention. For example, although the illustrated embodiment relies on movement of the liquid across a side boundary wall of the container in which it is held, it is also possible to arrange an internal partition to provide a path for the displacement of the liquid. Also, although the illustrated embodiment utilises the interface between a pair of plate members for capillary action on the volatile material other forms of capillary passage can be provided, including a multiplicity of discrete passages.

What is claimed is:

1. Dispensing apparatus for a volatile liquid comprising a container having a substantially closed interior space for the liquid and at least one capillary passage for communication with an exterior extending from an upper region of the interior space adjacent an upper portion only of an upwardly extending wall or partition, whereby only liquid displaced onto the upper portion of said wall or partition can reach said at least one capillary passage to be drawn therethrough to be released from the container, wherein the container is mounted on a support in an upright position but is tiltable thereon by a transverse inertia force in a same direction as a direction of displacement of the liquid.

2. Apparatus according to claim 1, wherein the container is supported on a mounting so as to be tiltable about an axis below a center of gravity of the container and return means urging the container to an upright position on the mounting against any tilting force experienced by the container.

3. Apparatus according to claim 2, further comprising means for limiting tilting displacement of the container on the support.

4. Apparatus according to claim 3, wherein said tilting displacement is limited to give the container wall or partition a minimum angle of not substantially less than 15° to a horizontal.

5. Apparatus according to claim 2, wherein the container is held on the support by resilient means urging the container downwards onto the support.

6. Apparatus according to claim 5, wherein the container is rotationally symmetrical and is held by said resilient means to be tiltable in any direction transverse to an axis of symmetry of the container.

7. Apparatus according to claim 6, wherein the resilient means maintain a bearing contact between the container and the support that moves laterally away from a tension element with increasing tilt.

8. Apparatus according to claim 6, wherein said at least one capillary passage occupies a substantially annular area and extends around a periphery of the interior space at the upper region.

9. Apparatus according to claim 8, wherein communication with the exterior is at a center of an annulus of said at least one passage, with an emanator at said center for said liquid.

10. Apparatus according to claim 8, wherein the container comprises a bowl with a peripheral side wall sloping upwards from a central region forming lateral boundaries of the interior space.

11. Apparatus according to claim 1, wherein said at least one capillary passage is formed at an interface of a pair of abutting planar surfaces.

12. Apparatus according to according to claim 1, wherein the container comprises a bowl with a peripheral side wall sloping upwards from a central region forming lateral boundaries of the interior space.

13. Apparatus according to claim 12, wherein said at least one capillary passage occupies a substantially annular area and extends around the periphery of the interior space at the upper region.

14. Apparatus according to claim 12, wherein the bowl has a half-cone angle not substantially less than 25°.

15. Apparatus according to claim 1, further comprising a filling tube extending into the container interior space from the upper region to limit a filling level therein.

16. Apparatus according to claim 1, further comprising an internal space above said at least one capillary passage for holding liquid clear of said at least one passage with the container inverted.

17. Dispensing apparatus for a volatile liquid comprising a container having a substantially closed interior space for the liquid and annular capillary passage extending across an upper region of the interior space adjacent an upper portion of an upwardly extending side wall of the container symmetrically around the container, and an emanator in contact with said passage at a center of an annulus of said passage, whereby only liquid displaced onto said upper wall portion can reach the capillary passage to be drawn therethrough to the emanator and dispensed therefrom, wherein the container is rotationally symmetrical and is held by resilient means to be tiltable in any direction transverse to an axis of symmetry.

18. Apparatus according to claim 17, wherein the annular capillary passage is planar.

* * * * *